(12) United States Patent
Bacus (10) Patent No.: US 7,833,698 B2
(45) Date of Patent: Nov. 16, 2010

(54) METHOD FOR DETERMINING THE RESPONSE TO CANCER THERAPY

(75) Inventor: Sarah S. Bacus, Hinsdale, IL (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/760,119

(22) Filed: Jan. 12, 2001

(65) Prior Publication Data

US 2001/0044124 A1 Nov. 22, 2001

Related U.S. Application Data

(60) Provisional application No. 60/176,514, filed on Jan. 12, 2000, provisional application No. 60/176,515, filed on Jan. 12, 2000.

(51) Int. Cl.
| | |
|---|---|
| G01N 33/48 | (2006.01) |
| G01N 33/53 | (2006.01) |
| G01N 33/573 | (2006.01) |
| G01N 33/567 | (2006.01) |
| G01N 33/574 | (2006.01) |
| G01N 33/577 | (2006.01) |

(52) U.S. Cl. .............................. 435/4; 435/7.1; 435/7.4; 435/7.92; 436/63; 436/64; 436/503

(58) Field of Classification Search ..................... 435/4; 436/64, 501
See application file for complete search history.

(56) References Cited

U.S. PATENT DOCUMENTS

| | | | | |
|---|---|---|---|---|
| 4,741,043 | A * | 4/1988 | Bacus ......................... | 382/129 |
| 5,389,523 | A * | 2/1995 | Plant et al. ................. | 435/7.92 |
| 5,498,522 | A * | 3/1996 | Porter ........................ | 435/6 |
| 5,536,642 | A * | 7/1996 | Barbera-Guillem et al. ...... | 435/7.23 |
| 5,665,549 | A * | 9/1997 | Pinkel et al. .................... | 435/6 |
| 5,772,998 | A * | 6/1998 | Dasch et al. ............. | 424/133.1 |
| 5,852,035 | A * | 12/1998 | Pamukcu | |
| 5,935,801 | A * | 8/1999 | Schlossman et al. | |
| 5,972,622 | A * | 10/1999 | Desjardins | |
| 6,350,452 | B1 * | 2/2002 | Riss | |
| 6,372,895 | B1 * | 4/2002 | Bentsen et al. ................ | 536/4.1 |
| 6,447,997 | B1 * | 9/2002 | Los et al. ........................ | 435/6 |
| 2004/0058320 | A1 * | 3/2004 | Roninson et al. ............... | 435/6 |

FOREIGN PATENT DOCUMENTS

| | | | |
|---|---|---|---|
| WO | WO 99/16789 | * | 4/1999 |
| WO | WO 99/24620 | * | 5/1999 |

OTHER PUBLICATIONS

The abstract of Bacus et al (Breast Cancer research and Treatment, 1999, vol. 57, p. 55).*
Warri et al (Journal of the National cancer Institute, 1993, vol. 85, pp. 1412-1418.*
The abstract of Fornier et al (Oncology, 1999, vol. 13, p. 647-658.*
The abstract of Lebwhol et al (Annals of Oncology, 1999, 10 suppl. 6, pp. 139-146).*
Caffo et al (Clinical Cancer research, 1996, vol. 2, pp. 1591-1599.*
The abstract of el-Deiry et al (Cancer Research, 1995, vol. 55, pp. 2910-2919).*
The abstract of Thor et al (Journal of the National cancer Institute, 1992, vol. 84, pp. 845-855).*
The abstract of Shetty et al (Leukemia Research, 1996, vol. 20, pp. 11-12).*
Hochhauser (Anti-Cancer Drugs, 1997, vol. 8, pp. 903-910).*
The abstract of Ohtani et al (Cancer, 1999, vol. 85, pp. 1711-1718).*
The abstract of Emig et al (British Journal of Cancer, 1998, vol. 78, pp. 1661-1668).*
Meyn et al (Anticancer Drugs, 1995, vol. 6, pp. 443-450).*
The abstract of Booth et al (Apoptosis, 1996, vol. 1, pp. 191-200).*
The abstract of Shen et al (Cancer, 1998, vol. 82, pp. 2373-2381).*
The abstract of Hiraishi et al, Glycobiology, 1993, vol. 3, pp. 381-390).*
The abstract of Cutrona et al(Journal of Experimental Medicine, 1995, vol. 181, pp. 699-711).*
The abstract of Frankfurt et al (anticancer Research, 1996, vol. 16, pp. 1979-1988).*
The abstract of Attallah et al (Hepato-Gastroenterology, 1996, vol. 43, pp. 1305-1312).*
The abstract of Smith and al-Mounhri (Biomed Pharmacother, 1998, vol. 52, pp. 116-121).*
The abstract of Vollmer et al (Cancer Research, 1992, vol. 52, pp. 4642-4648).*
The abstract of Dannecker et al (Ann Oncol, 1996, vol. 7, pp. 391-395).*
The abstract of Kopp et al (Cancer Research, 1995, vol. 55, pp. 4512-4515).*
Sasaki et al (Jpn J Cancer Research, 1998, vol. 89, pp. 562-570).*
The abstract of Srivastava et al (Anticancer Res, 1998, vol. 18, pp. 4003-4010).*
The abstract of Gillett et al. (J Pathol. Jan. 1999;187(2):200-6).*
The abstract of Emig et al (Br J Cancer. 1998, vol. 78, pp. 1661-1668).*
DeVita (Cancer, Principles & Practice of Oncology, 2001, pp. 345-356).*
Morris et al (Biochemical and Molecular Medicine, 1997, vol. 60, pp. 108-115).*
Abstract of Sethi et al (Proc Annu Meet Am Soc Clin Oncol, 1996, vol. 15, pp. A1308).*
Urashima et al (Blood, 1997, vol. 90, pp. 4106-4115).*
Wang et at (International Journal of Oncology, 1999, vol. 15, pp. 1097-1102).*
Li et al (Leukemia and Lymphoma, 1994, vol. 13, suppl. 1, pp. 65-70).*
Abstract of Cen et al, Zhonghua nei ke za zhi [Chinese Journal of Internal Medicine] 1997, vol. 36, pp. 300-303.*
Cohen et al (Biochemical Society Symposium, 1998, vol. 63, pp. 199-210).*

(Continued)

Primary Examiner—Karen A Canella
(74) Attorney, Agent, or Firm—McDonnell Boehnen Hulbert & Berghoff LLP (57) ABSTRACT

The invention relates to a method for determining the response to cancer therapy in an individual using image analysis.

16 Claims, 4 Drawing Sheets

OTHER PUBLICATIONS

Abstract of Bacus et al (Proc Annu Meet Am Assoc Cancer Res, 1996, vol. 37, A3945).*

Chang et al (Cancer Research, 1999, vol. 59, pp. 3761-3767).*

Eymin et al (Oncogene, 1999, vol. 18, pp. 1411-1418).*

Dragnev et al, The Oncologist, 2000, vol. 5, pp. 361-368.*

Dimiri et al, PNAS, 1995, vol. 92, pp. 9363-9367.*

Park et al (Journal of Cancer Research and Clinical Oncology, 2000, vol. 126, pp. 455-460).*

Butta et al (Cancer Research, 1992, vol. 52, pp. 4261-4264).*

Comerci et al (Clinical Cancer Research, 1997, vol. 3, pp. 157-160).*

Cada et al Ed.s, Drug Facts and Comparisons, 1999, p. 3283.*

Bacus et al., "Neu differentiation factor (Heregulin) activates a p53-dependent pathway in cancer cells," Oncogene 12(12):2535-47, 1996.

Chang et al., "$p21^{Waf1/Cip1/Sdi1}$-induced growth arrest is associated with depletion of mitosis-control proteins and leads to abnormal mitosis and endoreduplication in recovering cells," Oncogene 19:2165-2170, 2000.

Kopp et al., "Transforming Growth Factor β2 (TGF-β2) Levels in Plasma of Patients with Metastatic Breast Cancer Treated with Tamoxifen," Cancer Research 55(20):4512-4515, 1995.

Lei et al., "The expression of suppressor gene p16, p21 and p53 in nasopharyngeal carcinoma," Lin Chuang Er Bi Yan Hou Ke Za Zhi 13(9):406-8, 1999.

Meyn et al., "Apoptosis in murine tumors treated with chemotherapy agents," Anti-Cancer Drugs 6:443-450, 1995.

Shibata et al., "Suppression of mammary carcinoma growth in vitro and in vivo by inducible expression of the Cdk inhibitor p21," Cancer Gene Therapy 8:23-35, 2001.

Timmermann et al., "Re-expression of endogenous $p16^{ink4a}$ in oral squamous cell carcinoma lines by 5-aza-2'-deoxycytidine treatment induces a senescence-like state," Oncogene 17(26):3445-53, 1998.

Dannecker et al.; Induction of TGF-beta by an antiprogestin in the human breast cancer cell line T-47D; Ann. Onc., Apr. 1996; 7: 391-395.

Gillett et al.; Cyclin-dependent kinase inhibitor p27Kip1 expression and interaction with other cell cycle-associated proteins in mammary carcinoma; J Pathol, Jan. 1999; 187(2): 200-6.

Smith et al.; Primary chemotherapy in breast cancer, Biomed Pharmacother, Jan. 1998; 52(3): 116-21.

Srivastava et al.; Growth inhibition and activation of apoptotic gene expression by human chorionic gonadotropin in human breast epithelial cells; Anticancer Res, Nov. 1998; 18(6A): 4003-10.

Vollmer et al.; Down-regulation of tenascin expression by antiprogestins during terminal differentiation of rat mammary tumors; Cancer Res., Sep. 1992; 52: 4642-4648.

\* cited by examiner

METHOD FOR DETERMINING THE RESPONSE TO CANCER THERAPY

This application is a continuation of U.S. Provisional Patent Application Nos. 60/176,514 and 60/176,515, each filed on Jan. 12, 2000, the disclosure of each of which is explicitly incorporated by reference herein.

BACKGROUND OF THE INVENTION

1. Field of the Invention

The invention relates to methods for determining or predicting response to cancer therapy in an individual. In particular, the invention relates to methods for using image analysis to assess the efficacy of chemotherapeutic and chemopreventative agents in a human in need of treatment with such agents by detecting expression levels of biological makers associated with senescence, apoptosis or terminal differentiation. More specifically, the invention provides methods where the amount of the senescence, apoptosis or terminal differentiation marker is quantitated in tissue and cell samples removed from an individual before and after exposure to the chemotherapeutic or chemopreventative agent.

2. Background of the Invention

A primary goal of cancer therapy is to selectively kill or inhibit the uncontrolled growth of malignant cells while not adversely affecting normal cells. Traditional chemotherapeutic agents are highly cytotoxic agents that preferably have greater affinity for malignant cells than for normal cells, or at least preferentially affect malignant cells based on their high rate of metabolic activity. However, these agents often harm normal cells.

In the use of anticancer drugs, monoclonal antibodies, or chemopreventive agents, growth arrest, terminal differentiation and cell death of the cancerous or precancerous cells is intended (Mendelsohn, 1990, *Semin. Cancer Biol.* 1:339-44; Hancock et al., 1991, *Cancer Res.* 51:4575-80; Arteaga et al., 1994, *Cancer Res.*, 54:3758-65; Pietras et al., 1994, *Oncogene* 9:1829-38; Bacus et al., 1997, *Anal. Quant. Cytol. Histol.* 19:316-28; Bacus et al., 1999, *Breast J.*; Baselga et al., 1999, Proceedings of AACR NCI EORTC International Conference, Abstract 98; Cobleigh et al., 1999, *J. Clin. Oncol.* 17:2639-48; DiGiovanna, 1999, *PPO Updates: Princ. Practice Oncol.* 13:1-9; Hortobagyi, 1999, *J. Clin. Oncol.* 17:25-29; Shak, 1999, *Semin. Oncol.* 26:71-77; Sliwkowski et al., 1999, *Semin. Oncol.* 26:60-70; Vincent et al., 2000, *Cancer Chemother. Pharmacol.* 45: 231-38). Drug-induced growth arrest or cell death is often characterized by morphological and biochemical changes associated with programmed cell death or terminal differentiation (as opposed to mitotic cell death).

Although chemotherapeutic drugs can be administered at doses high enough to bring about cell death, such doses typically produce deleterious effects on normal as well as tumor cells. Differentiating agents, and lower doses of chemotherapeutic drugs and agents frequently results in growth arrest rather than cell death; such arrest can be followed by apoptosis and sell death, or continued proliferation once the chemotherapeutic drugs are withdrawn. Administration of cytotoxic and chemotherapeutic drugs or ionizing radiation may also induce transient growth arrest, a state which depends largely on the function of p53 and a p53-regulated cyclin-dependent kinase inhibitors (such as p16, p27, and p19) or growth inhibitors (such as TGF-β, IL-4, and IL-6). Upon removal of the chemotherapeutic drug, cells subjected to the drug treatment will eventually resume division and either continue to proliferate or die. Some drug-treated tumor cells undergo prolonged growth arrest and fail to resume cell division upon release from the drug.

In normal cells, terminal proliferation arrest may result from terminal differentiation or replicative senescence. Senescence is a physiological process that limits the proliferative span of normal cells. A commonly-used marker of senescence in human cells is expression of senescence-associated β-galactosidase (SA-β-Gal). This protein has been shown to correlate with senescence in aging cell cultures in vitro and with cells in vivo. Terminal proliferation arrest in normal cells can be rapidly induced by treatment with DNA-damaging drugs or γ-irradiation and is accompanied by the morphological features of senescence and the induction of SA-β-Gal. Accelerated senescence is likely to be a protective response of cells to carcinogenic impact. Similar to other damage responses of normal cells—such as quiescence and apoptosis—senescence-like terminal proliferation arrest involves the function of proteins such as wild-type p53 and the up-regulation of such proteins as $p21^{WAF1}$, p16, p19, and p27 (Kwok and Sutherland, 1989, *J. Natl. Cancer Inst.* 81:1020-24; Kwok and Sutherland, 1991, *Int. J. Cancer* 49:73-76; Kastan et al., 1991, *Cancer Res.* 51:6304-11; Lane, 1992, *Nature* 358:15-16; Kuerbitz et al., 1992, *Proc. Natl. Acad. Sci. U.S.A.* 89:7491-95; Gu et al., 1993, *Nature* 366:707-10; Halevy et al., 1995, *Science* 267:1018-21; Sherr and Roberts, 1995, *Genes Dev.* 9:1149-63; Luo et al., 1995, *Nature* 375:159-61; Dimri et al., 1995, *Proc. Natl. Acad. Sci. U.S.A.* 92:9363-67; Bacus et al., 1996, *Oncogene* 12:2535-47; Liu et al., 1996, *Cancer Res.* 56:31-35; Wang et al., 1998, *Oncogene* 17:1923-30; Chang et al., 1999, *Oncogene* 18:4808-18; Hong et al., 1999, *Cancer Res.* 59:2847-52; Sionov and Haupt, 1999, *Oncogene* 18:6145-57; Wouters et al., 1999, *Oncogene* 18:6540-45).

Tumor cells appear to have retained the ability to enter senescence and terminal proliferation arrest. Treatment of tumor cells with different classes of agents that affect cell differentiation, and anticancer agents, readily induces morphological, enzymatic, and other changes characteristic of senescence (such as the up-regulation of p53, p21, p27, p16, TGF-β, IL-4, IL-6, and SA-β-Gal). This senescence-like phenotype (SLP) distinguishes cells that will become stably growth-arrested from cells that will recover from drug exposure and continue to proliferate. Thus, the induction of senescence-like terminal proliferation arrest provides an important determinant of treatment response in tumor cells.

Apoptosis is generally regarded as an active suicidal response to various physiological or pathological stimuli. Recent studies have shown that a variety of DNA-damaging agents, including X-ray irradiation and several chemotherapeutic drugs (e.g., alkylating agents and topoisomerase II inhibitors) cause necrosis or initiate pathways leading to apoptosis. The exact mechanism by which apoptosis is induced by these agents is not yet known. However, expression of the suppressor gene p53 has been implicated in this process (Kwok and Sutherland, 1989, *J. Natl. Cancer Inst.* 81:1020-24; Kwok and Sutherland, 1991, *Int. J. Cancer* 49:73-76; Lane, 1992, *Nature* 358:15-16; Kuerbitz et al., 1992, *Proc. Natl. Acad. Sci. U.S.A.* 89:7491-95; Luo et al., 1995, *Nature* 375:159-61; Liu et al., 1996, *Cancer Res.* 56:31-35; Mellinghoff and Sawyers, 2000, *PPO Updates* 14:1-11). In addition, the up-regulation of caspases (e.g., caspase 9 or caspase 3) or their chaperone molecules (e.g., heat shock protein 60) has been associated with apoptosis.

In cells undergoing apoptosis, DNA-damaging stimuli can result in an elevation of intracellular p53 protein levels. Increased levels of wild-type p53, in turn, inhibit the cell cycle at $G_1$, thus permitting the damaged cell to undergo DNA repair. However, if the damaged cell is unable to undergo DNA repair, p53 can trigger programmed cell death. It is this ability to trigger programmed cell death that contributes to the induction of tumor cell death following exposure to chemotherapeutic agents.

Increased levels of p53 can also lead to the activation of a number of genes that contain wild-type p53-binding sequences, including the MDM-2 oncogene, Bax, and the WAF1/CIP1 gene. The WAF1/CIP1 gene encodes a protein having a $M_r$ of 21,000 that associates with cyclin-Cdk complexes and is capable of inhibiting kinase activity associated with these complexes. A major target of WAF (p21 or CIP) inhibition is the cyclin E-Cdk2 kinase complex whose activity is required for $G_0$ to S phase cell cycle progression. The WAF1/CIP1 gene is transcriptionally activated in response to DNA-damaging agents that trigger $G_1$ arrest or apoptosis in cells with wild-type p53 but not in tumor cells harboring deletions or mutations of the p53 gene. However, WAF1/CIP1 has also been shown to be up-regulated in cells undergoing differentiation or cell cycle arrest by a p53-independent mechanism.

Thus, there are a variety of cellular markers of senescence, apoptosis and terminal proliferative arrest that can be used to detect the effects of chemotherapeutic and chemopreventative drugs and agents. These markers can be used to assess the success or failure of any particular chemotherapeutic or chemopreventative drug or agent, or combination thereof, to affect an anticancer effect on tumor cells in vivo.

In contrast to traditional anticancer methods, where chemotherapeutic drug treatment is undertaken as an adjunct to and after surgical intervention, neoadjuvant (or primary) chemotherapy consists of administering drugs as an initial treatment in cancer patients. One advantage of such an approach is that, in primary tumors of more than 3 cm this approach permits the use of conservative surgical procedures (as opposed to, e.g., mastectomy in breast cancer patients) in the majority of patients. Another advantage is that for many cancers, a partial and/or complete response is achieved in about two-thirds of all cases. Finally, since the majority of patients are responsive after two to three cycles of chemotherapeutic treatment, it is possible to monitor the in vivo efficacy of the chemotherapeutic regimen employed, which is important for a timely identification of those cancers which are non-responsive to chemotherapeutic treatment. Timely identification of non-responsive tumors, in turn, allows the clinician to limit the cancer patient's exposure to unnecessary side-effects and institute alternative treatments.

The efficacy of chemotherapeutic agents in treating particular cancers is unpredictable. In view of this unpredictability, it has not been possible to determine, prior to starting therapy, whether one or more selected agents would be active as anti-tumor agents or to render an accurate prognosis of course of treatment in an individual patient. It would be very desirable to be able to determine the efficacy of a proposed therapeutic agent (or combination of agents) in an individual patient. There is a need in the art for a method of assessing the efficacy of chemotherapeutic programs that is both time- and cost-effective and minimally traumatic to cancer patients.

SUMMARY OF THE INVENTION

The present invention provides methods for determining the response to cancer therapy in an individual. The invention specifically provides methods for assessing efficacy of chemotherapeutic and chemopreventative agents in a human in need of treatment with such agents by detecting expression levels of biological makers associated with senescence, apoptosis or terminal differentiation. In the inventive methods, the amount of one or a plurality of senescence, apoptosis or terminal differentiation markers is quantitated in tissue and cell samples removed from an individual before and after exposure to the chemotherapeutic or chemopreventative agent. In preferred embodiments, the amount of said marker is determined using image analysis of immunohistochemically-stained tissue or cell samples obtained from a patient tumor.

In one embodiment of the inventive methods, response to a chemotherapeutic or chemopreventive agent in an individual is determined by collecting a first tissue or cell sample from the individual before exposing the individual to the chemotherapeutic or chemopreventive agent, collecting a second tissue or cell sample from the individual after exposing the individual to the chemotherapeutic or chemopreventive agent, immunohistochemically staining the first and second tissue or cell samples using a detectably-labeled antibody directed against a biological marker associated with senescence, apoptosis or terminal differentiation, determining the amount of the marker in the first and second tissue or cell samples, and determining whether expression of the biological marker associated with senescence, apoptosis or terminal differentiation was increased following exposure to the chemotherapeutic or chemopreventive agent. In a preferred embodiment, the detectable label is a chromagen or a fluorophore.

Specific preferred embodiments of the present invention will become evident from the following more detailed description of certain preferred embodiments and the claims.

DETAILED DESCRIPTION OF THE PREFERRED EMBODIMENTS

The methods of the present invention are useful for determining the response to cancer therapy in an individual. Specifically, the present invention provides methods for assessing the efficacy of treating an individual in need of such treatment with a chemotherapeutic or chemopreventive agent, in which the level of expression of a biological marker associated with senescence, apoptosis or terminal differentiation is quantitated in immunohistochemically-stained tissue or cell samples removed from the individual before and after exposure to the chemotherapeutic or chemopreventive agent. In preferred embodiments, expression levels are quantitated using computer-aided image analysis system.

In one embodiment of the methods of this invention, response to a chemotherapeutic or chemopreventive agent in an individual is determined by collecting a first tissue or cell sample from the individual before exposing the individual to the chemotherapeutic or chemopreventive agent, collecting a second tissue or cell sample from the individual after exposing the individual to the chemotherapeutic or chemopreventive agent, immunohistochemically staining the first and second tissue or cell samples using a detectably-labeled antibody directed against a biological marker associated with senescence, apoptosis or terminal differentiation, determining amount of expression of one or a plurality of biological markers associated with senescence, apoptosis or terminal differentiation in the first and second tissue or cell samples, and determining whether expression of the biological marker(s) associated with senescence, apoptosis or terminal differentiation was increased following exposure to the chemotherapeutic or chemopreventive agent.

In preferred embodiments, biological markers whose expression is induced or increases in cellular senescence, apoptosis and terminal differentiation may include but are not limited to p21, p27, p16, TGF-β, IL-4, IL-6, and SA-β-Gal, generally and collectively known as the senescence-like phenotype (SLP). This senescence-like phenotype (SLP) can be used to distinguish cells with restricted proliferative potential from those that continue to proliferate after drug exposure, suggesting that senescence-like terminal proliferation arrest is an important determinant of treatment response in human cancer.

In cells treated with cytotoxic drugs, SLP induction and cell death appear to be concurrent and independent responses. Thus, both SA-β-Gal$^+$ cells and SA-β-Gal$^-$ cells have a similar probability of undergoing mitotic death during drug treatment or within days following release from the drug. Once the rapid process of cell death is completed, however, SLP can be used to distinguish growth-retarded and non-clonogenic cells from recovering and proliferating cells. The overall outcome of treatment with chemopreventive or chemotherapeutic drugs is therefore determined by a combination of factors responsible for the induction of cell death (mitotic cell death or apoptosis) and senescence-like terminal proliferation arrest.

Exposure to moderate doses of doxorubicin induces SLP. However, when patients are treated with other agents, such as Taxol or Taxoter, apoptosis and up-regulation of p53 and p21 become more evident. The same is true when patients are treated with Herceptin™, a monoclonal antibody to the oncogenic receptor HER-2/neu. Thus, SLP induction may be the primary determinant of treatment outcome for cytostatic differentiating agents such as retinoids, and other chemopreventive agents. In addition, image analysis may be used to examine therapeutic response by quantitating the expression of proteins that are involved in activated pathways (e.g., phosphorylated MAP kinase and Akt) in tissues before and after treatment with kinase inhibitors.

Analysis of SLP markers such as β-Gal, p53, and p21 in clinical cancer may provide an important diagnostic approach for monitoring tumor response to different forms of therapy and can be done by calibrated staining for various factors associated with senescence and quantified by microscope based image analysis.

In a specific embodiment of the methods of the present invention, cells are removed from an individual before and after treatment with a putative anti-cancer agent and the cells are fixed using, e.g., paraformaldehyde. Cell samples are then treated with an organic solvent, such as acetone, formalin, or methanol, to render the cells permeable for immunohistological staining. Methods of fixation are known to those of skill in the art.

Where the presence and distribution of p53, p21, p16, p27, or p21-WAF1 protein are determined, the proteins are identified using suitable antibody systems such as sandwich systems using a primary antibody that specifically binds to the protein of interest and a secondary antibody that binds to the primary antibody. The antibody system can then be visualized using suitable stains (Bacus et al., 1999, *Breast J.*). Generally, antibodies and other molecules that specifically bind to these target proteins are known in the art, and the methods of the present invention can be practiced using any antibody or other molecule or collection of molecules that specifically binds to any of said biological markers of senescence, apoptosis or terminal differentiation.

Exemplary primary antibodies that bind to p53, p21, and p16 include the monoclonal antibody Ab-2 (Oncogene Sciences, Cambridge, Mass.). Similarly, exemplary antibodies that bind to p21 protein include the monoclonal antibody Ab-1 (Oncogene Sciences). An exemplary secondary antibody that may be used with either of these primary antibodies is rabbit anti-mouse IgG (Jackson Labs, West Grove, Pa.). After exposure to antibodies, an enzyme complex such as ABC complex (Vector Labs, Burlington, Calif.) is added to complete the antibody sandwich system and render it amenable to staining and counterstaining. Image analysis techniques are used to complete the quantitation.

Figure 1A:
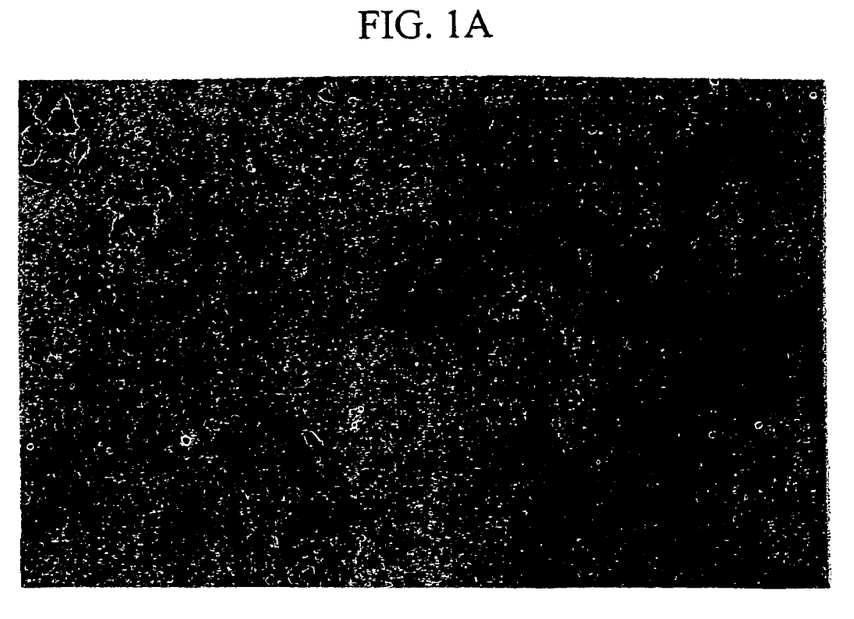
FIGS. 1A-1B show the results of analysis of MCF7 cells that were not treated (A) or treated (B) with doxorubicin, and then stained for SA-β-Gal activity.
Figure 1B:
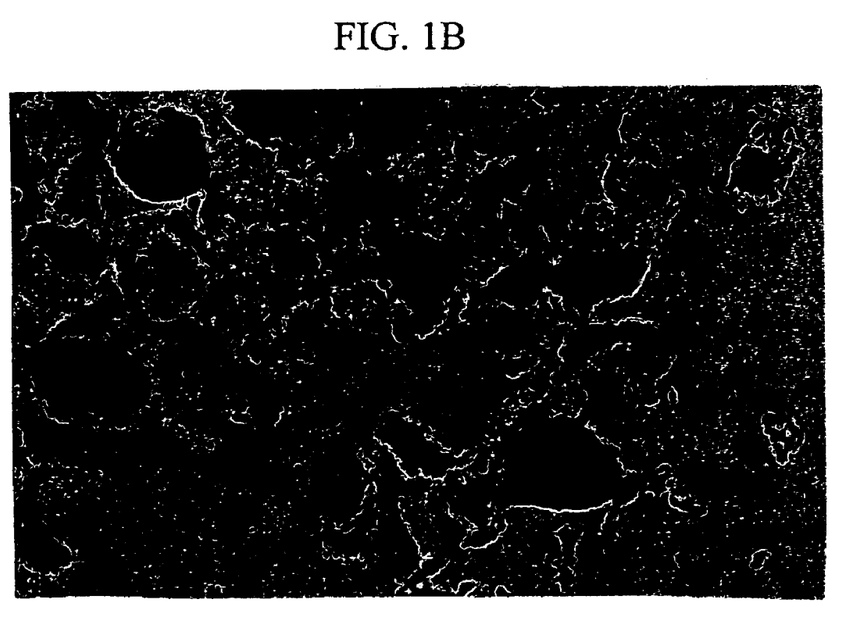
Figure 2A:
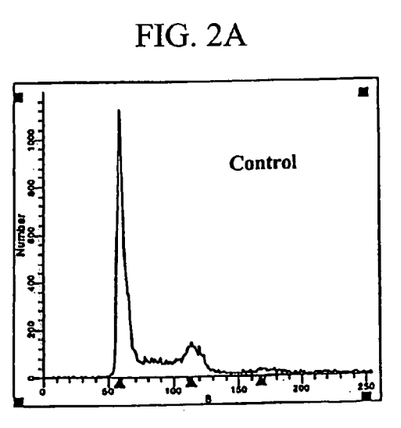
FIGS. 2A-2C show the results of flow cytometric analysis of MCF7 cells untreated (A) or treated (B) with doxorubicin, or treated with Taxol (C)
Figure 2B:
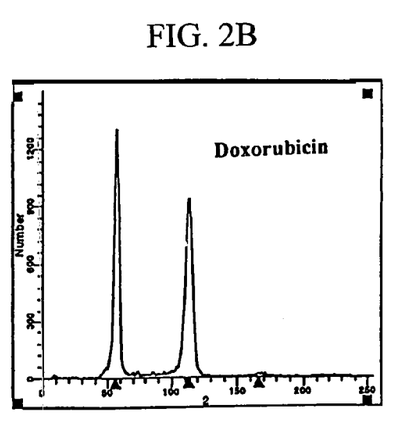
Figure 2C:
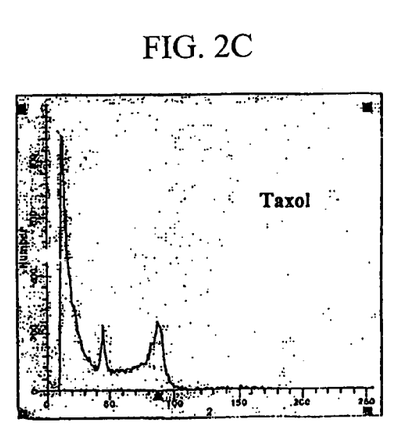
Figure 3A:
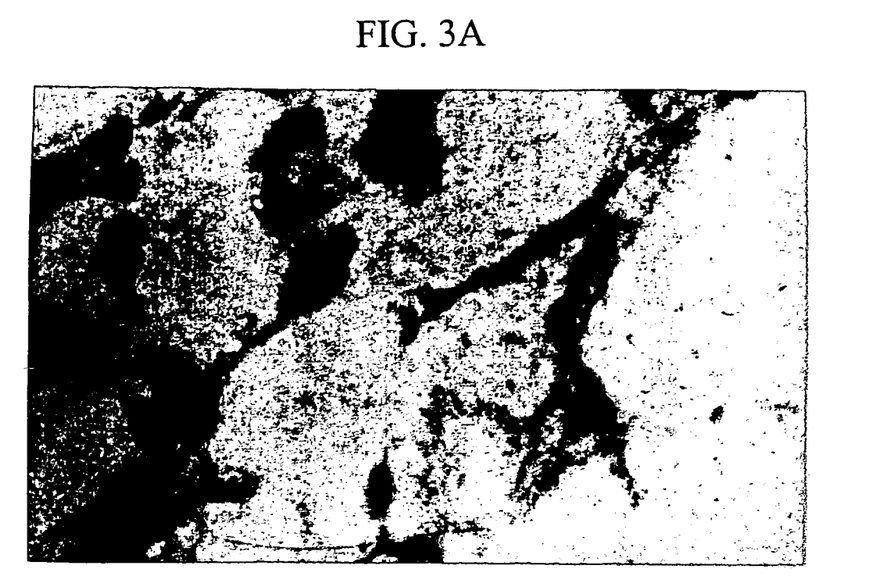
FIGS. 3A-3C illustrate the results of an analysis of a tumor sample removed from an individual following treatment with Herceptin™ (an antibody to the oncogene protein HER-2/neu). Tumor tissue was stained with either Hemotoxin and Eosin (A), SA-β-Gal (24 hours after treatment with Herceptin™; C), or SA-β-Gal 14 days after treatment with Herceptin™.
Figure 3B:
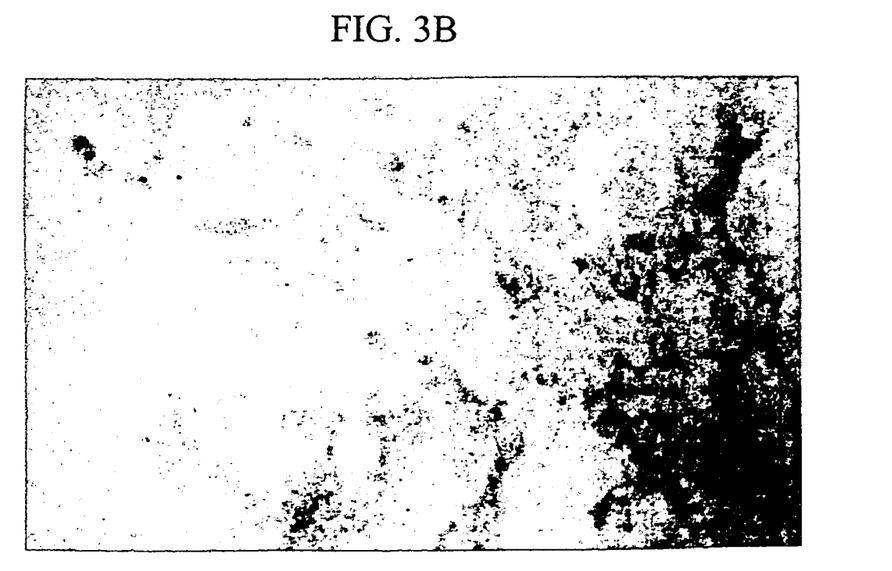
Figure 3C:
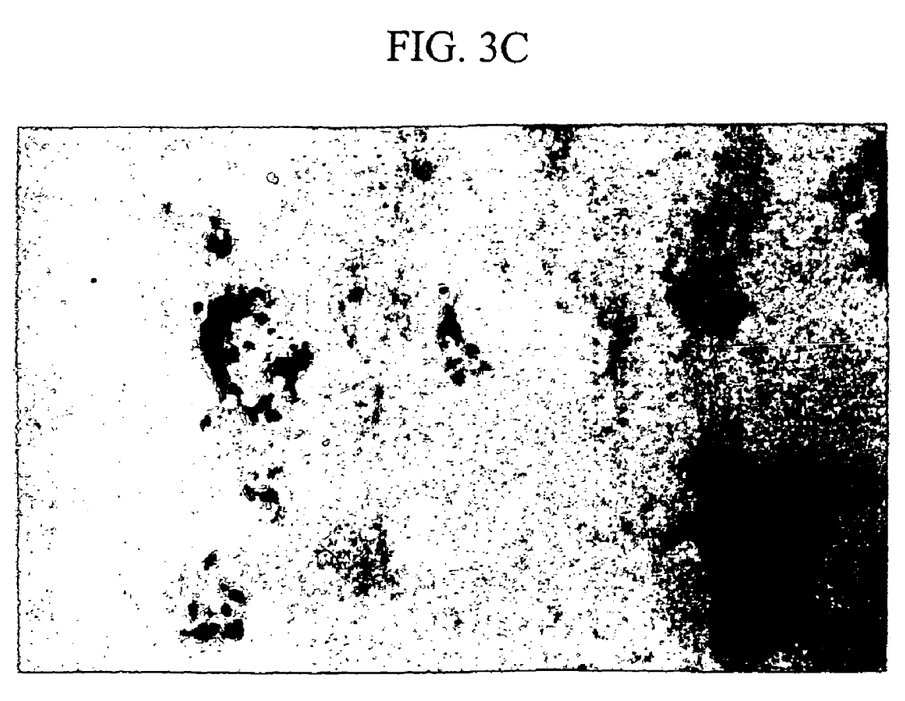

The preferred embodiment of the method of the present invention and its advantages over previously investigated methods for quantitating the response to cancer therapy are best understood by referring to FIGS. 1-3 and Examples 1-6. The Examples, which follow, are illustrative of specific embodiments of the invention, and various uses thereof. They are set forth for explanatory purposes only, and are not to be taken as limiting the invention.

EXAMPLE 1

β-Galactosidase (β-Gal) Staining

Cells were washed in PBS, fixed for 3-5 minutes at room temperature in 2% formaldehyde and 0.2% glutaraldehyde (or in 3% formaldehyde alone), washed, and incubated at 37° C. in fresh senescence-associated β-Gal (SA-β-Gal) staining solution (1 mg/ml 5-bromo-4-chloro-3-indolyl β-D-galactoside (X-Gal), 20 mg/ml dimethylformamide; 40 mM citric acid/sodium phosphate, pH 6.0; 5 mM potassium ferrocyanide; 5 mM potassium ferricyanide; 150 mM NaCl; 2 mM $MgCl_2$. Staining was evident following 2-4 hours of incubation and maximal staining was reached after in 12-16 hours. To detect lysosomal β-Gal, the staining solution was prepared with citric acid/sodium phosphate at pH 4.0 (Baselga et al., 1999, Proceedings of AACR NCI EORTC International Conference, Abstract 98).

EXAMPLE 2

Quantitation of Protein Expression by Computer-Aided Image Analysis

The expression of proteins associated with senescence or apoptosis are quantitated by image analysis using a suitable primary antibody (such as Ab-2 for p53, or Ab-1 for WAF1, HSP60, or caspase 3), secondary antibody (such as rabbit anti-mouse IgG), and tertiary ABC complex.

Tertiary ABC complexes are visualized by treating the sections with diaminobenizidine (DAB) stain under appropriate conditions. In a second step, the tissue is counterstained with another optical enhancement factor, preferably ethyl green. The resulting preparation has green nuclei with varying degrees of brown diaminobenzidine (DAB) precipitate localized to the nuclei (and indicating the level of expression of p53, p21, p16, WAF1, HSP60, or caspase-3 protein). Although a staining technique using peroxidase and ethyl green is exemplary, other stains and optical enhancement factors are also suitable (such as alkaline phosphatase coupled with a specific chromagen such as Fast Red or Fast Green). Spectral studies have shown that the ethyl green stain offers good spectral separation from the DAB precipitate of the immunoperoxidase technique such that different features of the image can be readily separated by filtering at two different wavelengths. This allows the image to be digitized into two separate images, one in which all the cell nuclei are optically enhanced (ethyl green or Fast Green) and one in which only those tissue areas with receptor staining (DAB) are optically enhanced. In a preferred embodiment, the images can be separated by a 600 nanometer (red) filter to produce an image of the counterstained area and a 500 nanometer (green) filter to produce an image of the tissue areas staining with the DAB precipitate.

To further differentiate those areas, an interactive threshold setting technique can be used in which an operator visualizing the images can set a boundary on the areas under consideration. When the boundaries are set, the images are formed by eliminating all parts of the image that are below the threshold in optical density. A threshold is set for the first image, and a second threshold is set for the second image.

The image processing method then consists of first forming the mask image of the tissues under consideration with the red filter. This mask image is stored and another image for expressed protein quantification is then acquired by using the green filtered version of the same image. Using the filters in combination allows for the optical enhancement of those areas of the tissue mask where tissue components are stained with DAB (which are darkened) and those tissue components having only the green counterstain (which are lightened). An image analysis can then be performed using only those areas of the image that are stained and which are within the mask.

The amount of target protein is then quantitated by statistical analysis of the differences between the two images. Also, the proportion or percentage of total tissue area stained may be readily calculated, as the area stained above an antibody threshold level in the second image.

Red and green filters are suitable for practice of the invention. For SA-β-Gal, a green filter (500 nm) is used to determine the total cytoplasmic area stained with red eosin and compared with the blue area stained for SA-β-Gal (600 nm) as determined using a red filter. This implementation shows a convenient and advantageous method for discriminating between two areas having counterstaining. It is recognized that there are various other staining or optical enhancement methods and filtering methods which can be used to optically enhance one particular area or feature over another cell feature (such as Fast green and eosin). The specific examples provided herein are suggestive of other equivalents for visualization of cell nuclei containing expressed p53, WAF1 protein, and SA-β-Gal.

Following visualization of nuclei containing p53 protein or WAF1 protein, the percentage of such cells in tissue derived from patients after treatment may be compared to the percentage of such cells in untreated tissue.

From these comparisons, the potential effectiveness of a putative therapeutic or chemopreventive agent against the cancer may be determined. Specifically, if there is a greater percentage of cells expressing p53, WAF1, SA-β-Gal, HSP60, or caspase 3 in the treated portion of the sample than there is in the untreated portion of the sample, then the therapeutic agent used in the treatment will be predicted to be potentially an effective agent for treating the cancer. Conversely, if there is a substantially equal percentage of cells expressing SA-β-Gal, p53, WAF1, HSP60, or caspase 3 in both the treated and untreated portions of the sample, or there is less protein expression in the treated portion of the sample, then the putative therapeutic agent will not be predicted to be effective for treatment of the cancer.

U.S. Pat. Nos. 5,252,487 and 5,288,477, incorporated herein by reference, disclose one method of quantitating DNA and protein.

EXAMPLE 3

Response to Doxorubicin in Breast Cancer Cell Lines

Cellular changes are induced by treatment with moderate doses of doxorubicin and Taxol in breast tumor-derived human cell lines. MCF7 cells were treated for 2-3 days with 50 nM doxorubicin or Taxol (doses that induce growth inhibition and cellular death as measured by flow cytometry; as described by, e.g., Dolbeare et al., 1983, *Proc. Natl. Acad. Sci. U.S.A.* 80:5573-77) and then were stained for SA-β-Gal expression 10-11 days after release from the drug. The results of this treatment on the formation of sub-GI fraction and the SA-β-Gal$^+$ phenotype are shown in FIGS. 1A-1B and 2A-2C. Taxol-induced apoptosis is evident by the hypodiploid peak in the flow cytometry histogram, whereas doxorubicin treatment (and treatment with the monoclonal antibody Herceptin™) resulted in senescence and blocks at $G_1$, $G_2$, and $G_2M$ as seen in SA-β-Gal$^+$ cells having the morphological features of senescence (FIGS. 2A-2C and Tables I and II).

EXAMPLE 4

Quantitation of SA-β-Gal Expression Following Treatment with Herceptin™

Frozen tumor sections were fixed and then stained for SA-β-Gal expression. SA-β-Gal$^+$ cells were quantitated using bright-field microscopy and image analysis. Tissues were obtained from a patient receiving only Herceptin™. The first needle biopsy was obtained from the metastatic disease before initiation of Herceptin™ therapy. On day 1 the patient received 4 mg/1 g.v Herceptin™ for 10 minutes. A second biopsy was taken on day 2, 24 hours after the patient received a second Herceptin™ treatment. A third biopsy was taken on day 14, 24 hours after the patient received a third dose of Herceptin™. The results of SA-β-Gal quantitation are shown in FIGS. 3A-3C and Table II.

EXAMPLE 5

Quantitation of $p21^{WAF1}$ Expression Following Treatment with Doxorubicin

MCF7 cells were treated for 3 days with doxorubicin and then stained for p53 and $p21^{CIP1/WAF1}$ expression. Cells were cultured, stained, and analyzed as described above for SA-β-Gal using appropriate antibodies. The results of p53 and $p21^{CIP1/WAF1}$ quantitation are shown in Table III.

EXAMPLE 6

Quantitation of p21$^{WAF1}$ Expression in Individuals Following Chemotherapy Tissue samples from twenty breast cancer patients was analyzed for p21 expression by image analysis before and after neoadjuvant chemotherapy. Experiments were performed by the Imperial Cancer Research Fund (ICRF; Oxford University, U.K.). The results of this analysis show marked differences in tissue samples collected before and after treatment (Table IV).

It should be understood that the foregoing disclosure emphasizes certain specific embodiments of the invention and that all modifications or alternatives equivalent thereto are within the spirit and scope of the invention as set forth in the appended claims.

TABLE I

Percentage of Cells Expressing SA-β-Gal Cells

| Cells | Φ | Doxorubicin | Taxol |
|---|---|---|---|
| MCF7 | 2% | 24% | 13% |

TABLE II

Percentage of Cells Expressing SA-β-Gal in Patient Tissue After Herceptin Treatment

| Time Elapsed | Percent |
|---|---|
| Day 0 | 0% |
| Day 2 | 1.5% |
| Day 14 | 26% |

TABLE III

Expression of p53 and p21$^{CIP1/WAF1}$ in MCF7 Cells Treated for 3 days with Doxorubicin

| Treatment | Cells stained for p53 (% Cells) | Cells stained for p21$^{CIP1/WAF1}$ (% Cells) |
|---|---|---|
| Φ | 14.43 ± 6 | 10.61 ± 4 |
| DOX | 23.93 ± 7 | 50.81 ± 6 |

TABLE IV

Twenty Breast Cancer Patients Analyzed by Image Analysis Before and After Neoadjuvant Chemotherapy

| | P21− | P21+ |
|---|---|---|
| Before treatment | 16 | 4 |
| After treatment | 7 | 13 |

What is claimed is:

1. A method for determining a response to administration of a cancer chemotherapeutic agent to an individual, comprising:
   (a) collecting a first tissue or cell sample from the individual before exposing the individual to the cancer chemotherapeutic agent;
   (b) collecting a second tissue or cell sample from the individual after exposing the individual to the cancer chemotherapeutic agent;
   (c) staining the first and second tissue or cell samples with one or a multiplicity of stains to determine senescence-associated β-Gal (SA β-Gal) activity, p21 expression, or both SA β-Gal activity and p21 expression;
   (d) measuring the optical density of the stained tissue or cell samples in step (c), wherein the stained tissue or cell samples are illuminated with light having a wavelength absorbed by the one or a multiplicity of stains;
   determining whether SA β-Gal activity, expression of p21, or both SA β-Gal activity and expression of p21 was increased following exposure to the cancer chemotherapeutic agent.

2. The method of claim 1, wherein the p21 expression is determined with a detectably labeled antibody.

3. The method of claim 1, wherein the p21 expression is determined by ELISA assay.

4. The method of claim 1, wherein optical density of the stained tissue or cell samples is measured by image analysis.

5. The method of claim 4, wherein image analysis is performed by splitting a signal comprising the optical density of stained cells in the tissue or cell samples into a multiplicity of signals that are processed using optical filters having different absorption and transmittance properties, so that each signal is specific for the one or the multiplicity of stains used to stain the tissue or cell samples.

6. The method of claim 2, wherein the detectable label is a chromagen or a fluorophore.

7. The method of claim 1, wherein the tissue or cell samples are breast cancer tissue or cell samples.

8. The method of claim 1, wherein the chemotherapeutic agent comprises doxorubicin, trastuzamab (HERCEPTIN™), or paclitaxel (TAXOL™).

9. The method of claim 8, wherein the chemotherapeutic agent comprises doxorubicin.

10. A method for determining a response to administration of doxorubicin to an individual having breast cancer, comprising:
    (a) collecting a first tissue or cell sample from a breast cancer of an individual before exposing the individual to doxorubicin;
    (b) collecting a second tissue sample from a breast cancer of an individual after exposing the individual to doxorubicin;
    (c) detecting in the first and second tissue or cell samples SA β-Gal activity, p21 expression, or both SA β-Gal activity and p21 expression;
    (d) determining whether SA β-Gal activity, p21 expression, or both SA β-Gal activity and p21 expression was increased following exposure to doxorubicin.

11. The method of claim 10, wherein SA β-Gal activity, p21 expression, or a combination thereof is detected.

12. The method of claim 10, wherein detecting comprises staining the first and second tissue or cell samples for SA β-Gal activity, p21 expression, or both SA β-Gal activity and p21 expression, and measuring the optical density of one or more stained cells in the stained tissue or cell samples.

13. The method of claim 12, wherein the optical density of the one or more stained cells is measured by image analysis.

14. A method for determining a response to administration of doxorubicin to an individual having breast cancer, comprising:
    (a) collecting a first tissue or cell sample from a breast cancer of an individual before exposing the individual to doxorubicin;
    (b) collecting a second tissue sample from a breast cancer of an individual after exposing the individual to doxorubicin;

(c) detecting in the first and second tissue or cell samples p27 expression, p16 expression or both p27 expression and p16 expression;

(d) determining whether p27 expression, p16 expression or both P27 expression and p16 expression was increased following exposure to doxorubicin.

15. The method of claim 14, wherein detecting comprises staining the first and second tissue or cell samples for p27 expression, p16 expression or both p27 expression and p16 expression, and measuring the optical density of one or more stained cells in the stained tissue or cell samples.

16. The method of claim 15, wherein the optical density of the one or more stained cells is measured by image analysis.

* * * * *